United States Patent
Pruitt et al.

(10) Patent No.: US 10,323,226 B2
(45) Date of Patent: Jun. 18, 2019

(54) FEED MATERIAL FOR BIOMASS GENERATOR

(71) Applicant: NCH Corporation, Irving, TX (US)

(72) Inventors: Judith G. Pruitt, Mesquite, TX (US); Robert C. Pearce, III, Arlington, TX (US); Daniel Aberle, Irving, TX (US); Charles J. Greenwald, Dallas, TX (US); Gabriel F. K. Everett, Coppell, TX (US)

(73) Assignee: NCH Corporation, Irving, TX (US)

( * ) Notice: Subject to any disclaimer, the term of this patent is extended or adjusted under 35 U.S.C. 154(b) by 17 days.

(21) Appl. No.: 15/474,447

(22) Filed: Mar. 30, 2017

(65) Prior Publication Data

US 2018/0282685 A1     Oct. 4, 2018

(51) Int. Cl.
*C12N 1/20* (2006.01)
*C02F 3/34* (2006.01)
*C02F 103/00* (2006.01)

(52) U.S. Cl.
CPC ............... *C12N 1/20* (2013.01); *C02F 3/348* (2013.01); *C02F 2103/005* (2013.01)

(58) Field of Classification Search
None
See application file for complete search history.

(56) References Cited

U.S. PATENT DOCUMENTS

| | | | |
|---|---|---|---|
| 3,242,055 A | | 3/1966 | De Lucia |
| 3,728,445 A | * | 4/1973 | Bardani ............... A61K 9/2004 424/465 |
| 4,810,385 A | | 3/1989 | Hater et al. |
| 5,275,943 A | | 1/1994 | DiTuro |
| 5,283,059 A | | 2/1994 | Suzuki et al. |
| 5,401,501 A | | 3/1995 | Pratt |
| 5,426,024 A | | 6/1995 | Flores-Cotera et al. |
| 5,447,866 A | | 9/1995 | Runyon |
| 5,516,687 A | | 5/1996 | Perez et al. |
| 5,716,630 A | | 2/1998 | Lin et al. |
| 5,770,079 A | | 6/1998 | Haase |
| 5,911,877 A | | 6/1999 | Perez et al. |
| 5,998,184 A | | 12/1999 | Shi |
| 6,190,591 B1 | | 2/2001 | van Lengerich |
| 6,254,886 B1 | | 7/2001 | Fusca et al. |
| 6,280,719 B1 | | 8/2001 | Suh |
| 6,325,934 B1 | | 12/2001 | Tobey, Jr. et al. |
| 6,335,191 B1 | | 1/2002 | Kiplinger et al. |
| 6,544,552 B2 | * | 4/2003 | Sparks ................. A61K 9/0056 424/441 |
| 6,562,585 B1 | | 5/2003 | Hiatt |
| 6,620,611 B2 | | 9/2003 | Hince |
| 6,723,526 B1 | | 4/2004 | Hernandez et al. |
| 6,733,781 B2 | | 5/2004 | Abu-Izza et al. |
| 7,029,699 B2 | | 4/2006 | Robinson et al. |
| 7,037,708 B1 | | 5/2006 | Runge et al. |
| 7,081,361 B2 | | 7/2006 | Pearce, III et al. |
| 7,785,646 B2 | | 8/2010 | Wong |
| 8,551,762 B2 | | 10/2013 | Fleming et al. |
| 2009/0111694 A1 | | 4/2009 | Dituro |
| 2013/0171204 A1 | * | 7/2013 | DuBourdieu ........ A61K 9/0056 424/400 |
| 2015/0079661 A1 | | 3/2015 | Pruitt et al. |
| 2017/0073632 A1 | | 3/2017 | Pruitt et al. |

FOREIGN PATENT DOCUMENTS

| | | |
|---|---|---|
| CN | 1768744 | 5/2006 |
| WO | WO2013142792 | 9/2013 |

OTHER PUBLICATIONS

Anonymous. Soy Sauce: Dehydrated, downloaded from https://web.archive.org/web/20101124174704/http://kikkonnanusa.com/foodmanufacturers/products_fm_sub.php?fam=302 on Jun. 13, 2018. (Year: 2010).*

Anonymous. Calories in Kikkoman Soy Sauce and Nutrition Facts; FatSecret, downloaded from https://www.fatsecret.com/calories-nutrition/kikkoman/soy-sauce on Jun. 13, 2018. (Year: 2018).*

Anonymous. Defatted Soy Flour Commodity Fact Sheet; USAID downloaded from https://www.usaid.gov/what-we-do/agriculture-and-food-security/food-assistance/resources/defatted-soy-flour-commodity-fact on Jun. 14, 2018. (Year: 2016).*

Persistence Market Research, Soy Sauce Powder Market: Global Industry Analysis and Forecast 2016-2024, Mar. 14, 2017 [retrieved on May 1, 2018]. Retrieved from the Internet: <URL:http://web.archive.org/web/20170314224429/hattp://www.persistencemarketresearch.com:80/market-research/soy-sauce-powder-market.asp.

Xu et al., Production of alkali-tolerant cellulase-free xylanase by *Pseudomonas* sp. WLUN024 with wheat bran as the main substrate, published 2005 in the World Journal of Microbiology and Biotechnology, vol. 21, pp. 575-581.

* cited by examiner

Primary Examiner — Sharmila G Landau
Assistant Examiner — Paul C Martin
(74) Attorney, Agent, or Firm — Ross Barnes LLP; Robin L. Barnes

(57) ABSTRACT

A bacteria starter material for use in biomass generators without causing jamming of the feeder mechanism, particularly under high temperature and/or high humidity conditions, the starter material comprising one or more species of waste-decomposing bacteria, sucrose, and a soy based protein. Preferably, DI-PAC® sugar (sucrose and maltodextrin) and powdered KIKKOMAN® Soy Sauce are used as the sugar and protein ingredients. The starter material may also comprise a dried bran culture comprising *Pseudomonas*. The starter material ingredients are blended together and formed into a tablet or pellet having a particular shape, size, and hardness characteristics suitable for use in the feeder mechanism of a biomass generator.

26 Claims, No Drawings

FEED MATERIAL FOR BIOMASS GENERATOR

BACKGROUND OF THE INVENTION

1. Field of the Invention

The present invention relates generally to tableted blends comprising at least one waste-decomposing microorganism, soy protein, and sugar for use as a starter material for biomass generators, particularly suitable for high humidity environments.

2. Description of Related Art

Bacteria decompose organic materials in the environment in a natural process that typically degrades organic material into carbon dioxide and water. Under normal conditions, competition for resources, limited supplies of nutrients, and natural enemies can combine to inhibit rapid bacterial growth that in turn limits organic material decomposition. Bacteria proliferate rapidly when selected strains of bacteria are isolated and provided a growth-promoting food source. These larger bacterial populations decompose waste material more quickly and effectively and can be used in a wide variety of applications, such as, for example, in septic tanks, grease traps, drains, RV holding tanks, cesspools, lagoons, ponds, outdoor toilets, portable toilets and the like, which tend to collect waste present in various forms such as proteins, carbohydrates (such as cellulose), and lipids such as fats and oils.

Solutions containing utility populations of waste-decomposing bacteria may be grown at or near a site requiring treatment using a biomass generator, such as those disclosed in U.S. Pat. Nos. 6,335,191, 7,081,361, 8,551,762, and other patents citing or cited in them. These biomass generators use a starter material comprising at least one selected beneficial bacterial strain and enough of a suitable bacteria food source to grow the bacteria from a small starter population to a utility population that is large enough to sustain growth and promote a desired end use application when discharged from this device into a treatment site containing waste material or other media containing another viable food source. Typically, the starter material is fed from a storage canister into a growth chamber in the biomass generator and water is added. The bacteria are allowed to grow for a growth period, usually around 24 hours. After the growth period, the high population bacteria solution is discharged from the growth chamber to the area needing treatment, such as a drain or grease trap. Then another amount of starter material is fed into the growth chamber and the process is repeated. Generally, there is enough starter material in a canister to supply the biomass generator for around one month before the starter material needs to be replenished.

Conventional, commercially available sources of starter bacteria are available in liquid or solid form. Some starter bacteria are already combined with a starter nutrient and others require mixture with a separate starter nutrient, most often in an aqueous suspension. Solid starter materials are preferred over liquids because they provide a bacteria starter population in a form that provides stable storage, easier handling, and low overall cost. However, many solid starter materials also have drawbacks. For examples, powdered starter materials tend to float on the surface of the water in the growth chamber rather than mixing with the water to allow the bacteria to grow. Powdered starter materials also tend to get jammed in the automated feed mechanisms of the biomass generators, particularly under humid conditions. Some tablet or pellet forms of starter materials also tend to break apart in the feed mechanism, causing jamming and premature activation of the bacteria. Other tablet or pellets forms of starter material can be too hard, either getting crushed into a powder in the feed mechanism or not breaking apart fast enough inside the growth chamber.

The commercially available Free Flow tablets were developed to address several of these issues. Free Flow tablets comprise a dried bran culture containing *Pseudomonas*, one or more *Bacillus* species without a carrier, and a blend of nutrients, including proteins, starches, and sugars in a tablet form having a specified shape and hardness, as described in U.S. Patent Application Publication No. 2015/0079661 (incorporated herein by reference), for use in biomass generators. During use, the Free Flow tablets are often exposed to high heat and humidity conditions, which have resulted in structural issues with the tablets, including swelling and tablets that stick together, which result in jamming the feeder mechanism in the biomass generator. There is a need for an improved starter material tablet or pellet composition that maintains structural integrity under high heat and humidity conditions.

SUMMARY OF THE INVENTION

One preferred embodiment of a bacteria starter material composition according to the invention suitable for use in a biomass generator, particularly under conditions involving high temperature and humidity, comprises at least one *Bacillus* species, a soy protein, sugar and starch. More preferably, the soy protein is a protein hydrolyzed by *Aspergillus oryzae*. Most preferably, the soy protein is the commercially available Kikkoman Powdered Soy Sauce. According to another preferred embodiment, the bacteria starter material further comprises sucrose or maltodextrin or a combination thereof as the sugar. Most preferably, the sugar is the commercially available DI-PAC® sugar from American Sugar Company/Domino Sugar, which is a mixture of sucrose and maltodextrin. According to another preferred embodiment, a bacteria starter material of any embodiment described herein also comprises one or more of the following: a sodium salt; a calcium salt; a phosphate salt; a nitrogen compound; soda; a buffering agent; tablet starch; a binder; and a dried bran culture comprising bran and *Pseudomonas*. Most preferably, the bacteria starter material is in a tablet or pellet form with the size and shape and tablet characteristics described in U.S. Patent Application Publication No. 2015/0079661.

One preferred method for making bacteria starter material in pellet or tablet form according to the invention comprises: the following steps: (1) grinding the sucrose (or DI-PAC® sugar) to a mesh size suitable for forming tablets (if needed), preferably with mean particle sizes indicated below; (2) grinding the other ingredients (including the bran culture bacteria, but not any *Bacillus* spores, which are already small) to a mesh size of around USS 20 to 30 (if necessary); (3) blending the protein, starch, and sugar, preferably for around 10 minutes; (4) blending in all other ingredients, preferably for around 10 minutes; (5) using a tablet press to form tablets or pellets with appropriately shaped and sized dies. More preferably, the sucrose (or DI-PAC® sugar) is ground to particle sizes so that no more than 3% is USS 40, no more than 8% is USS 200, and at least 75% is USS 100 to have a mean particle size around USS 100, if grinding is needed to obtain these particle sizes. Another preferred method for making a bacteria starter material comprising a dried bran culture (such as EcoBionics Bran Culture) comprises the following additional steps prior to the grinding of the dried bran culture in step 2 above: (a) autoclaving bran (preferably bran flakes) to remove background contamination (which could compete with the desired bacteria and could be harmful to the water system or other area being treated by the biomass generator), preferably at a temperature of around 121° C. and a pressure of 15 p.s.i. for around 1.5 hours; (b) applying *Pseudomonas* cells as inoculum in a liquid *Pseudomonas* growth medium to the autoclaved bran flakes; (c) incubating the bran culture under humidity for around 24 to 48 hours; and (d) drying the *Pseudomonas* bran culture for around 72 hours, preferably to a water activity of around 0.6 or lower.

Bacteria starter material according to preferred composition embodiments and preferred methods of the invention have the benefit of maintaining structural integrity of the tablet or pellet in the feed container and through the feed mechanism of an automated or semi-automated biomass generator under higher temperature and/or higher humidity conditions, while maintaining bacteria viability through the tableting process and during storage in the biomass generator prior to delivery to the growth tank. The preferred embodiments do not cause jamming of the feeder mechanism, do not swell under high temperature or high humidity conditions, the tablets or pellets do not stick to each other, and are not as susceptible to premature bacteria activation (prior to reaching the growth tank) compared to prior art starter materials, including the previous version of the Free Flow tablets described in U.S. Patent Application Publication No. 2015/0079661. Feed materials in tablet form according to preferred embodiments of the invention maintain structural stability and do not stick to other tablets of the same feed material when stored at temperatures between around 40 F and around 115 F.

Feed materials in tablet form according to preferred embodiments of the invention also maintain structural stability and do not stick to other tablets of the same feed material when stored at relative humidity levels between around 0% and around 67%.

DETAILED DESCRIPTION OF THE INVENTION

The present invention is a bacterial and nutrient delivery composition and method of making the composition in tablet or pellet form for use in a biomass generator. The preferred compositions according to the invention are structurally stable during storage and in the feed container and feed mechanism of a biomass generator, particularly under high temperature and/or high humidity conditions, but readily dissolvable in the growth tank of the biomass generator.

One preferred embodiment of a bacteria starter material composition according to the invention comprises at least one *Bacillus* species, a soy protein, a sugar and a starch. More preferably, the soy protein is a protein hydrolyzed by *Aspergillus oryzae*. Protein hydrolyzed by *Aspergillus oryzae* is preferred over acid hydrolysis of soy, but acid hydrolyzed soy may also be used. Most preferably, the soy protein is the commercially available KIKKOMAN® Powdered Soy Sauce or a tamari soy product. A whole soy protein, such as Baker's NUTRISOY® soy, may also be used. The protein source used in the prior art Free Flow tablets is casein, which undergoes acid hydrolysis resulting in fewer of the amino acids being bioavailable for use as a growth promoting nutrient for the bacteria species in the starter material. The KIKKOMAN® Soy and tamari soy are both hydrolyzed by *Aspergillus oryzae* rather than acid hydrolysis, which results in a much greater percentage (approaching 100%) of the amino acids being bioavailable. Preferably, the bacteria starter material comprises around 2-7% by weight soy protein and more preferably around 5% of the powdered KIKKOMAN® Soy Sauce.

According to another preferred embodiment, the bacteria starter material further comprises sucrose or maltodextrin or a combination thereof as the sugar. Most preferably, the sugar is the commercially available DI-PAC® sugar from American Sugar Company/Domino Sugar, which is a mixture of around 96.25-97.75% sucrose and 2.25-3.75% maltodextrin. Preferably, the bacteria starter material comprises around 25-40% by weight of one or more sugars, more preferably between around 35% to 40% of a combination of sucrose and maltodextrin. The sugar source used in the prior art Free Flow tablets is dextrose. The use of around 35% dextrose was found to aid in achieving the right compressibility for tablet formation. However, dextrose is susceptible to the Maillard reaction, or caramelization. The beginning step of the Maillard reaction is the condensation of a carbonyl group, in this case from the reducing monosaccharide glucose, with a free amino acid group. When the prior art Free Flow tablets with dextrose were exposed to higher temperatures and higher humidity conditions during storage or use in a biomass generator, the Maillard reaction compromises the structure of the tablets resulting in swollen, soft tablets that stick together and clump. This impedes proper functioning of the feed mechanism in the biomass generator, so that the starter material does not make it to the growth chamber to grow into a utility population and requiring servicing of the biomass generator unit. The use of sucrose avoids the structural issues associated with dextrose because sucrose is not as susceptible to carmelization, while retaining the necessary compressibility for tablet formation. Sucrose is a non-reducing disaccharide that has to be broken up into its constituent monosaccharides via hydrolysis before it could undergo caramelization. By using sucrose, and most preferably the DI-PAC® combination of sucrose and maltodextrin, the bacteria starter material tablets according to this preferred embodiment are structurally stable after 30 days at 45 C and 67% relative humidity. At 45-49 C, the prior Free Flow tablets with dextrose were swollen and melted together after only three days.

According to another preferred embodiment, a bacteria starter material of any embodiment described herein also comprises one or more of the following: a sodium salt; a calcium salt; a phosphate salt; a nitrogen compound; soda; a buffering agent; tablet starch; a binder; and a dried bran culture comprising bran and *Pseudomonas*. Most preferably, the bacteria starter material comprises each of these ingredients in the following amounts by weight:

TABLE 1

Raw Materials for Bacteria Starter Tablet/Pellet

| Raw Material | Amount |
| --- | --- |
| Starch | 15-30% |
| Sucrose (or Sucrose and Maltodextrin) | 25-40% |
| Soy Protein | 2-7% |
| Sodium Salt | 1-2% |
| Calcium Salt | 0.1-1% |
| Soda | 3-7% |
| Buffering agent | 2-8% |
| Phosphate salt | 0.5-2.5% |
| Nitrogen compound | 2-7% |

TABLE 1-continued

Raw Materials for Bacteria Starter Tablet/Pellet

| Raw Material | Amount |
| --- | --- |
| Bran | 1-2% |
| Total bacteria | 0.1-10% |
| Tablet starch | 1-15% |
| Binder | 0.1-1% |

Most preferably, the bacteria starter material according to one preferred embodiment comprises each of these ingredients in the following amounts by weight:

TABLE 2

Preferred Raw Materials for Bacteria Starter Tablet/Pellet

| Raw Material | Amount |
| --- | --- |
| Corn Starch | 24.00% |
| Di-Pac Sugar | 35.30% |
| Kikkoman Soy Sauce (powdered) or Tamari Soy (powdered) | 5.00% |
| Sodium Chloride | 2.60% |
| Calcium Sulfate | 0.80% |
| Sodium Bi-carbonate | 6.40% |
| Disodium Phosphate | 6.00% |
| Monosodium Phosphate | 2.00% |
| Urea | 5.70% |
| EcoBionics Bran Culture (bran and *Pseudomonas* culture) | 1.20% |
| Spore Blend (*Bacillus* species and table salt) | 0.10% |
| Microcrystalline cellulose | 10.70% |
| Magnesium Stearate | 0.20% |

"Spore Blend" in Table 2, is about 60%-40% bacteria (of which it comprises around 33% AT31 *Bacillus subtilis*, 33% AT316 *Bacillus licheniformis*, 17.5% AT3032 *Bacillus subtilis*, and 17.5% AT3040 *Bacillus thuringiensis*) and about 40%-60% table salt. Other suitable cultures known to one of ordinary skill in the art may also be used. The *Bacillus* strains are preferably spray-dried without any carrier material to achieve a dry spore powder raw material. Compositions according to preferred embodiments of the invention may further comprise fillers, binders, and buffers and other materials, such as talc, lactose, highly dispersed silica, polyvinylpyrrolidone, cellulose powder, mannitol, sorbitol, xylitol, glucose, fructose, maltose, dextrose, kaolin or cellulose derivatives such as methylcellulose, hydroxylpropylcellulose or hydroxypropylmethylcellulose, starch (including various forms such as pre-gelatinized), light anhydrous silicic acid, titanium oxide, magnesium aluminometasilicate and polyethylene glycols, as well as calcium carbonate, calcium, magnesium or glyceryl stearate. Additional proteins such as casein or other suitable amino acids and their peptide polymers and derivatives thereof, including various nitrogenous compounds, may also be used. Various sodium and calcium salts such as sodium chloride, sodium bicarbonate, disodium phosphate, monosodium phosphate, calcium monohydrogen phosphate, and calcium sulfate may also be used. Various oils, including hydrogenated and partially hydrogenated oils, may be used. Any suitable colorant may also be used. The tablet compositions of the present invention may also comprise additives usually incorporated into tablet compositions to aid in the tablet forming process or in stabilizing the tablets for storage.

The bacteria starter material compositions according the invention are preferably formed into tablets or pellets. When making tablets, it is generally important to have a substantially uniform ingredient particle size to achieve a tablet that would be suitable for use in a biomass generator by being hard enough to not break apart in the feeder mechanism, but still break apart fairly quickly once in contact with water in the growth chamber. However, when sucrose is used according to preferred embodiments of the invention, it is important that the particle size for the sucrose be significantly smaller than the size of the other ingredients because sucrose is lighter than dextrose and does not form into tablets as readily. Preferably, the sucrose used has a mean particle size of around USS 100 and more preferably no more than 3% of the sucrose is USS 40, no more than 8% is USS 200, and at least 75% is USS 100. The sucrose may be ground if needed and is preferably put through a grinder with other materials to achieve a USS 20-30 mesh maximum ingredient size. More preferably the sucrose has a maximum of around 2-5%, and most preferably around 3%, 50 mesh particle size and a maximum of around 5%-10%, and most preferably around 8%, 200 mesh particle size. These particle size parameters for sucrose are important to achieving proper tablet formation and necessary tablet hardness, and to maintaining tablet integrity at higher temperatures and humidity levels. The remaining ingredients (except *Bacillus* spores, which are already small) are also put through a grinder and have a maximum particle size of USS 20-30 mesh.

One preferred method for making a bacteria starter material according to the invention comprises the following steps: (1) grinding the sucrose (or DI-PAC®) to a mesh size according to the ranges discussed above; (2) grinding the other ingredients (including the bran culture bacteria, but preferably not the *Bacillus* spores which are already small) to a mesh size of around 20 to 30 (if necessary); (3) blending the protein, starch, and sugar, preferably for around 10 minutes; (4) blending in all other ingredients, preferably for around 10 minutes; (5) using a tablet press to form tablets or pellets with appropriately shaped and sized dies. Another preferred method for making a bacteria starter material comprising a dried bran culture (such as EcoBionics Bran Culture) comprises the following additional steps prior to the grinding of the dried bran culture in step 2 above: (a) autoclaving bran (preferably bran flakes) to remove background contamination (which could compete with the desired bacteria and could be harmful to the water system or other area being treated by the biomass generator), preferably at a temperature of around 121° C. and a pressure of 15 p.s.i. for around 1.5 hours; (b) applying *Pseudomonas* cells as inoculum in a liquid *Pseudomonas* growth medium to the autoclaved bran flakes; (c) incubating the bran culture under humidity for around 24 to 48 hours; and (d) drying the *Pseudomonas* bran culture for around 72 hours, preferably to a water activity of around 0.6 or lower. The incubation period allows the *Pseudomonas* to grow (multiplying from around $1\times10^8$ cfu/gm of bran when initially applied to the bran to around $5\times10^9$ cfu/g after growth in the *Pseudomonas* bran culture) and form a biofilm that will help protect it through the rest of the manufacturing process. The drying prevents any residual contamination (bacteria, yeast, or mold) on the *Pseudomonas* bran culture from growing. The dried bran culture is then ground like the other ingredients to the preferred mesh size range. The grinding step is important because non-spore forming bacteria grown on bran are irregular in shape, densities, and sizes, which is not ideal for tableting. Grinding the dried *Pseudomonas* bran culture provides particles that are substantially uniform in size and shape, which allows tablet formation without requiring the use of excessive pressure that would damage the bacteria.

To reduce the mesh size of the bacteria ingredients (*Bacillus* (if needed) and/or *Pseudomonas* in the dried bran culture), a Stokes' grinder (for example, a grinder such as a bar oscillating granulator) is preferred in part because of its lesser shear and lower heat rather than other grinder types, for instance, a rotary-type grinder where the shear forces are greater. All other ingredients, may be ground with either a Fitzmill (for example, Model IR520 Chilsonator®) or Stokes Grinder or any other grinder capable of reducing the size of the constituent particles to the preferred mesh size and minimize phase separation.

The components of the preferred embodiment presented in Table 2 are blended in a preferred manner, although others may be acceptable, as follows: corn starch, DI-PAC®, and KIKKOMAN® Soy Sauce (powdered) are mixed in a blender for 10 minutes, followed by the addition of sodium chloride, calcium sulfate, sodium bicarbonate, disodium phosphate, monosodium phosphate, urea, microcrystalline cellulose, Spore Blend, and EcoBionics Bran Culture (all pre-ground, if needed, as previously described) and mixed for about 10 minutes. Magnesium stearate is also mixed with the composition and all mixing times are approximate and may be shortened or lengthened, depending upon the materials, the relative humidity, the mesh sizes, and other factors appreciated by one of ordinary skill. The final composition is then formed using a desired tablet press adapted with dies to obtain the preferred tablet shape described in U.S. Patent Application Publication No. 2015/0079661.

As used herein, the terms tablet and pellet are interchangeable unless one or the other is specifically excluded. Those of ordinary skill in the art will appreciate upon reading this specification, including the examples contained herein, that modifications and alterations to the composition and methodology for making the composition may be made within the scope of the invention and it is intended that the scope of the invention disclosed herein be limited only by the broadest interpretation of the appended claims to which the inventor is legally entitled.

We claim:

1. A biomass generator feed material in tablet form, the feed material comprising the following ingredients:
    at least one *Bacillus* species;
    a hydrolyzed soy protein;
    sucrose having a mesh size between 40 and 200; and
    starch.
2. The feed material of claim 1 wherein the ingredients are mixed throughout the tablet.
3. The feed material of claim 1 wherein the tablet has a substantially cylindrical shape with convex ends, a length-to-diameter-ratio between about 0.9 and about 1.2, and a cup depth between about 0.018 inches and about 0.048 inches.
4. The feed material of claim 1 wherein the tablet has a hardness between about 5.5 kilopond and about 8.5 kilopond.
5. The feed material of claim 1 further comprising a dried culture of bran and non-spore forming *Pseudomonas*.
6. The feed material of claim 5 wherein the *Bacillus* bacteria is one or more of *Bacillus subtilis, Bacillus licheniformis, Bacillus thuringiensis, Bacillus amyloliquefaciens*, or *Bacillus simplex*.
7. The feed material of claim 6 wherein the *Bacillus* bacteria is without a carrier.
8. The feed material of claim 5 wherein the *Bacillus* bacteria is without a carrier.
9. The feed material of claim 1 further comprising maltodextrin.
10. The feed material of claim 9 wherein the hydrolyzed soy protein comprises powdered soy sauce.
11. The feed material of claim 9 wherein the soy protein is hydrolyzed by a species of *Aspergillus*.
12. The feed material of claim 9 wherein the hydrolyzed soy protein is tamari soy.
13. The feed material of claim 1 wherein the tablet comprises around 2-7% hydrolyzed soy protein and around 25-40% sucrose by weight.
14. The feed material of claim 1 further comprising a dried culture of bran and non-spore forming *Pseudomonas* and wherein the tablet comprises around 0.1-10% of the *Pseudomonas* and *Bacillus* by combined weight.
15. The feed material of claim 1 wherein at least 75% of the sucrose has a mesh size of around 100 and wherein the hydrolyzed soy protein, starch, and dried bran culture have a mesh size between 20 and 30.
16. The feed material of claim 14 wherein the tablet comprises around 5% powdered soy sauce as the hydrolyzed soy protein and around 33% to 35% sucrose by weight.
17. The feed material of claim 16 wherein the starch is corn starch.
18. The feed material of claim 16 further comprising around 0.5% to 1.5% maltodextrin by weight.
19. The feed material of claim 18 further comprising around 10-15% microcrystalline cellulose by weight.
20. The feed material of claim 19 wherein the tablet comprises less than 2% bran by weight.
21. The feed material of claim 1 wherein the tablet maintains structural stability and does not stick to another tablet of the same feed material when stored at temperatures between around 40 F and around 115 F for up to 30 days.
22. The feed material of claim 1 wherein the tablet maintains structural stability and does not stick to another tablet of the same feed material when stored at relative humidity levels between around 0% and around 67% for up to 30 days.
23. The feed material of claim 1 wherein at least 75% of the sucrose has a mesh size of around 100.
24. The feed material of claim 11 wherein the hydrolyzed soy protein and starch have a mesh size between 20 and 30.
25. The feed material of claim 1 wherein the hydrolyzed soy protein is tamari soy.
26. The feed material of claim 1 wherein the soy protein is hydrolyzed by a species of *Aspergillus*.

* * * * *

UNITED STATES PATENT AND TRADEMARK OFFICE
CERTIFICATE OF CORRECTION

PATENT NO. : 10,323,226 B2  
APPLICATION NO. : 15/474447  
DATED : June 18, 2019  
INVENTOR(S) : Pruitt et al.

It is certified that error appears in the above-identified patent and that said Letters Patent is hereby corrected as shown below:

In the Claims

Column 8, Claim 15, Line 24 -- "claim 1" should read -- claim 14 --.

Column 8, Claim 24, Line 50 -- "claim 11" should read -- claim 1 --.

Signed and Sealed this
Eighteenth Day of August, 2020

Andrei Iancu
*Director of the United States Patent and Trademark Office*